United States Patent

Oren et al.

[11] Patent Number: 5,196,605
[45] Date of Patent: Mar. 23, 1993

[54] PROCESS FOR THE PREPARATION OF PURE 4,4'-DIHYDROXYBIPHENYL

[75] Inventors: Jakob Oren, Qiryat Bialik; Hugo Kesselman, Karmiel; Joshua Hermolin, Ramat-Hasharon, all of Israel

[73] Assignee: Bromine Compounds, Ltd., Beer-Sheva, Israel

[21] Appl. No.: 706,291

[22] Filed: May 28, 1991

[30] Foreign Application Priority Data

May 29, 1990 [IL] Israel ............................. 94554

[51] Int. Cl.$^5$ ................. C07C 39/14; C07C 37/70
[52] U.S. Cl. .......................... 568/730; 568/724; 568/717; 568/747; 568/748
[58] Field of Search ............ 568/722, 723, 724, 730, 568/747, 748, 728, 717

[56] References Cited

U.S. PATENT DOCUMENTS

| | | | |
|---|---|---|---|
| 3,413,341 | 11/1968 | Bursack | 568/730 |
| 4,340,768 | 7/1982 | Jinbo et al. | 568/730 |
| 4,853,487 | 8/1989 | Nonn | 568/730 |
| 4,891,452 | 1/1990 | Nonn et al. | 568/730 |

FOREIGN PATENT DOCUMENTS

| | | | |
|---|---|---|---|
| 0332203 | 9/1989 | European Pat. Off. | 568/724 |
| 3-038537 | 2/1991 | Japan | 568/730 |
| 3-038538 | 2/1991 | Japan | 568/730 |

Primary Examiner—Werren B. Lone
Attorney, Agent, or Firm—Michael N. Meller

[57] ABSTRACT

In a process for the preparation of 4,4'-dihydroxybiphenyl of high purity 4,4'-dibromobiphenyl is hydrolized in the presence of a copper compound catalyst, the insoluble materials comprising the catalyst is filtered off from the product mixture, 4,4'-dihydroxybiphenyl is precipitated by adjusting the pH and crude 4,4'-dihydroxybiphenyl separated from the product mixture is fractionally distilled to obtain substantially pure 4,4'-dihydroxybiphenyl.

15 Claims, 1 Drawing Sheet

PROCESS FOR THE PREPARATION OF PURE 4,4'-DIHYDROXYBIPHENYL

FIELD OF THE INVENTION

The present invention relates to a process for the preparation of 4,4'-dihydroxybiphenyl. More particularly, the invention relates to a purification process of 4,4'-dihydroxybiphenyl (DHBP) which is obtained by the hydrolysis of 4,4'-dibromobiphenyl (DBBP).

BACKGROUND OF THE INVENTION

The Prior Art 4,4'-dihydroxybiphenyl is a well known compound useful as a starting material for a variety of products such as dyes and resins, e.g., polyesters, polyepoxides, polyurethanes, polycarbonates and high performance polymers. The process for the preparation of DHBP is described in Japan Kokai 79-22347 (Hodogaya). The product obtained according to this patent was of low purity and was not suitable for most applications. In a later patent of the same applicant (U.S. Pat. No. 4,340,768) an improved process is described in which the crude product, obtained according to the process described in the aforementioned Japan Kokai, is purified by extracting 4-hydroxybiphenyl (4-HBP) from the product mixture with a suitable solvent and the remaining product solution is neutralized, crystallized, filtered and dried, yielding a product of a purity greater than 98% and containing less than about 30 ppm of inorganic salts. This patent indicates that "it is impossible to purify 4,4'-dihydroxybiphenyl by a distillation so as to give the quality required for the demands in view of the characteristics of 4,4'-dihydroxybiphenyl".

An alternative process for obtaining DHBP of high purity is described in U.S. Pat. No. 4,490,564 (Ethyl Corporation). According to this patent, the crude product is dissolved in an inert organic solvent, preferably at elevated temperatures. Water is then added to the inert organic solvent mixture which allows the inorganic salts that may be present to remain in the solution and the product to precipitate out. Although this procedure is allegedly technologically superior to that described in U.S. Pat. No. 4,340,768, the results in the examples do not substantiate this allegation, with respect to the final purity obtained. Additionally, the procedure of this patent is cumbersome, involving operations with organic solvents, filtration and drying.

Additional patents dealing with the production of DHBP using DBBP as raw material do not address in detail the problem of the purity of the product and purification processes therefore. Among these patents there are found U.S. Pat. No. 4,475,000 (Ethyl Corporation), French Patent Application FR 2,609,711 (Rhone-Poulenc Chemie), and EP 278,845.

SUMMARY OF THE INVENTION

It has now been surprisingly found, and this is an object of the present invention, that contrary to the teachings of U.S. Pat. No. 4,340,768, it is possible to obtain highly pure 4,4'-dihydroxybiphenyl by the fractional distillation of the crude product obtained by the hydrolysis of 4,4'-dibromobiphenyl.

It has further been surprisingly found, and this is another object of the invention, that it is possible to obtain by distillation of the crude DHBP a product which is of purity much higher than what is obtained in the prior art, and that this involves a relatively simple purification procedure without organic solvents, which is easier and less expensive than those known in the art.

DETAILED DESCRIPTION OF THE INVENTION

The process for the preparation of 4,4'-dihydroxybiphenyl according to the invention comprises the steps of:

hydrolyzing 4,4'-dibromobiphenyl in the presence of a copper compound catalyst;

filtering insoluble materials comprising the catalyst from the product mixture;

adjusting the pH of the resulting solution to a value of 9 or less, to precipitate crude 4,4'-dihydroxybiphenyl;

separating crude 4,4'-dihydroxybiphenyl from the product mixture; and fractionally distilling the crude 4,4'-dihydroxybiphenyl to obtain substantially pure 4,4'-dihydroxybiphenyl.

The first steps of the process may be steps known in the art. For instance, 4,4'-dihydroxybiphenyl can be prepared by hydrolyzing 4,4'-dibromobiphenyl in the presence of a copper compound catalyst in an aqueous alkaline solution at a temperature below 300° C., filtering the catalyst and insoluble compounds at the end of the reaction, precipitating the crude product by neutralizing or by acidifying the filtrate; separating the crude DHBP, e.g., by filtration, to yield a crude product which can be further processed by distillation.

Fractional distillation of the crude product should be carried out in a temperature and pressure range at which 4,4'-dihydroxybiphenyl does not sublime, namely, at a temperature range above the melting point of DHBP (284°-286° C.) and a pressure above 50 mmHg. At pressures below 40 mmHg sublimation takes place already at temperatures below the melting point of DHBP, and the impurities embedded in the product, which evaporate easily, as will be easily seen from Table I below, continuously contaminate the product and cannot be separated. At pressures between 40-50 mmHg the operation is not safe enough and it is not recommended to operate in this range. In addition, a serious technical problem arises from the fact that it is impossible to collect a large fraction of the sublimed material by cooling the exit to the pumping system and, therefore, the whole operation is doomed.

At pressures above 50 mmHg the above mentioned problems vanish and the resulting reflux allows a proper fractional distillation to take place. Too high pressure, on the other hand, are also not recommended. Operating at pressures higher than 200 mmHg, while possible, requires temperatures higher than 361° C., which lead to serious problems, such as a higher risk of product decomposition, operational and technological problems.

DESCRIPTION OF THE DRAWING

The vapor pressure of the different components of the crude DHBP product are shown in Table I below, and in FIG. 1.

TABLE I

Figure 1:
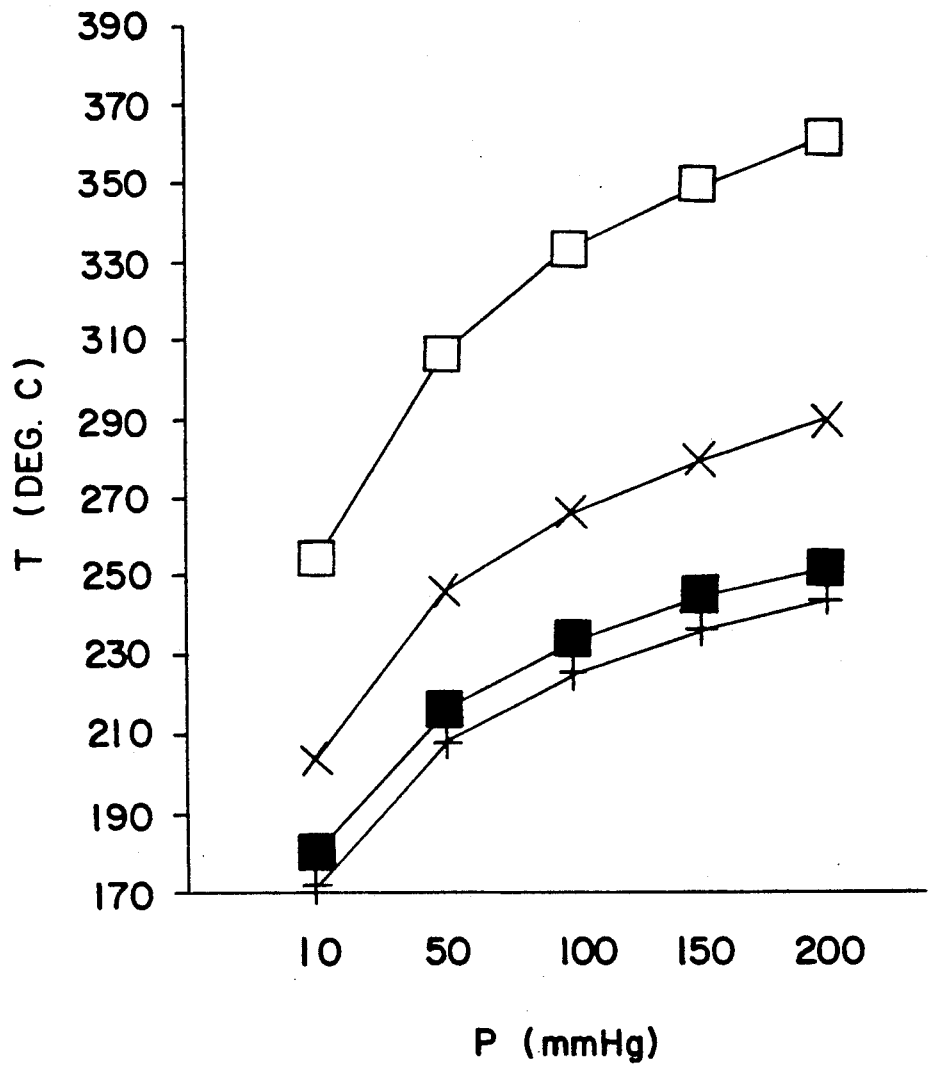

| P mm Hg | Temperature (°C.) | | | |
|---|---|---|---|---|
| | DHBP | 4-HBP | DBBP | 4-BBP |
| 10 | 254 | 180 | 203 | 172 |
| 50 | 306 | 215 | 245 | 208 |
| 100 | 333 | 233 | 266 | 225 |
| 150 | 349 | 244 | 279 | 236 |

TABLE I-continued

| P mm Hg | Temperature (°C.) | | | |
|---|---|---|---|---|
| | DHBP | 4-HBP | DBBP | 4-BBP |
| 200 | 361 | 251 | 289 | 244 |

DHBP = 4,4'-dihydroxybiphenyl
4-HBP = 4-hydroxybiphenyl
DBBP = 4,4'-dibromobiphenyl
4-BBP = 4-bromobiphenyl As will be understood by a person skilled in the art, it is essential in order to carry out the invention to employ in the fractional distillation temperatures and pressures at which 4,4'-dihydroxybiphenyl does not sublime. If these conditions are not met, then the distillation will not be successful. As will be appreciated by the skilled chemist, the purification process of the invention, employing fractional distillation, is much more convenient than the prior art processes inasmuch as no additional solvents are required, no extra stages are involved in the work-up procedure.

It should be noted that the intermediate 4-bromo-4'-hydroxybiphenyl is extremely reactive and it is substantially absent from the product mixture anyway. 2,4'-dihydroxybiphenyl does not present a problem, as no isomerisation takes place and it is absent from the starting DBBP.

The above and other advantages of the invention will be better understood through the following illustrative example of preferred embodiment.

EXAMPLE 1

A) Preparation of crude 4,4'-dihydroxybiphenyl

Into a 1.0 liter SS-316 autoclave there was placed a mixture of crude DBBP (93.6 g, 0.3 moles), aq. 6N NaOH (500 ml, 3.0 moles) and CuCl (2.0 g, 0.02 moles). The autoclave was sealed and heated to 260° C. A pressure of 450 psi was generated. Full conversion was achieved after 1 hour, after which the autoclave was cooled and opened. The reaction mixture was filtered to recover the catalyst. The filtrate was neutralized to pH 7 with 32% HCl, upon which crude DHBP precipitated and was separated by filtration. After drying 50 g crude DHBP was obtained.

B) Preparation of pure 4,4'-dihydroxybiphenyl 50 g of the dry, crude DHBP (obtained by the procedure of step (A)), containing 4.6% 4-HBP was heated to melting under nitrogen, then the pressure was reduced until reflux occurred. The distillation was performed at about 160 mmHg and no sublimation took place.

Two fractions were removed, the first of 7 g and the second of 40 g. The final temperature was about 352° C. The major fraction was found to contain >99.5% DHBP and the presence of metals was not detected.

According to a preferred embodiment of the invention, the wet cake obtained in the filtration stage of the process, which contains the copper compound catalyst, can be reused in a subsequent hydrolysis reaction without any further treatment.

EXAMPLE 2

Preparation of crude DHBP with recycled catalyst

Example 1 was repeated using 3.2 g of wet recovered catalyst, obtained by filtration from the previous experiment (Example 1), and 0.15 g CuCl which was added to compensate for the lost metal ion (giving a total of 0.02 moles Cu). The results obtained were as in Example 1.

We claim:

1. A process for the preparation of 4,4'-dihydroxybiphenyl of high purity, by treating a product mixture obtained from the hydrolysis reaction of 4,4'-dibromobiphenyl in the presence of a copper catalyst, further comprising the steps of:
   filtering insoluble materials comprising the catalyst from the product mixture;
   adjusting the pH of the resulting solution to a value of 9 or less, to precipitate crude 4,4'-dihydroxybiphenyl;
   separating crude 4,4'-dihydroxybiphenyl from the product mixture; and
   fractionally distilling the crude 4,4'-dihydroxybiphenyl to obtain substantially pure 4,4'-dihydroxybiphenyl.

2. A process according to claim 1, wherein the fractional distillation is carried out at a temperature which is above the melting temperature of 4,4'-dihydroxybiphenyl at the operating pressure.

3. A process according to claim 2, wherein the fractional distillation is carried out at a temperature in the range of 290°–400° C., and at a pressure of at least 50 mmHg.

4. A process according to claim 1, wherein the insoluble materials are separated from the product mixture by filtration.

5. A process according to claim 4, wherein the filtration of the crude product mixture is carried out after cooling below the boiling temperature.

6. A process according to claim 4, wherein the filter cake containing Cu is reused in a subsequent hydrolysis reaction as the catalyst without any further treatment.

7. A process according to claim 2, wherein the insoluble materials are separated from the product mixture by filtration.

8. A process according to claim 3, wherein the insoluble materials are separated from the product mixture by filtration.

9. A process according to claim 8, wherein the filtration of the crude product mixture is carried out after cooling below the boiling temperature.

10. A process according to claim 8, wherein the filtration of the crude product mixture is carried out after cooling below the boiling temperature.

11. A process according to claim 7, wherein the filter cake containing Cu is reused in a subsequent hydrolysis reaction as the catalyst without any further treatment.

12. A process according to claim 8, wherein the filter cake containing Cu is reused in a subsequent hydrolysis reaction as the catalyst without any further treatment.

13. A process according to claim 5, wherein the filter cake containing Cu is reused in a subsequent hydrolysis reaction as the catalyst without any further treatment.

14. A process according to claim 9, wherein the filter cake containing Cu is reused in a subsequent hydrolysis reaction as the catalyst without any further treatment.

15. A process according to claim 10, wherein the filter cake containing Cu is reused in a subsequent hydrolysis reaction as the catalyst without any further treatment.

* * * * *